(12) United States Patent
Keuchel et al.

(10) Patent No.: US 6,872,847 B2
(45) Date of Patent: Mar. 29, 2005

(54) PROCESS FOR THE PREPARATION OF ALKYL-N-(3-DIMETHYLAMINO) ALKYLCARBAMATES

(75) Inventors: Johannes Keuchel, Muhltal-Trautheim (DE); Günter Schlegel, Liederbach (DE)

(73) Assignee: Bayer Cropscience GmbH (DE)

( * ) Notice: Subject to any disclaimer, the term of this patent is extended or adjusted under 35 U.S.C. 154(b) by 0 days.

(21) Appl. No.: 10/476,706

(22) PCT Filed: Apr. 18, 2002

(86) PCT No.: PCT/EP02/05456

§ 371 (c)(1),
(2), (4) Date: Nov. 3, 2003

(87) PCT Pub. No.: WO02/090322

PCT Pub. Date: Nov. 14, 2002

(65) Prior Publication Data

US 2004/0152914 A1 Aug. 5, 2004

(30) Foreign Application Priority Data

May 3, 2001 (EP) ............................................. 01110711
Jun. 6, 2001 (EP) ............................................. 01113778

(51) Int. Cl.$^7$ ............................................... C07C 27/20
(52) U.S. Cl. ...................................................... 560/159
(58) Field of Search ........................................... 560/159

(56) References Cited

U.S. PATENT DOCUMENTS 5,304,650 A    4/1994   Krebs et al.

FOREIGN PATENT DOCUMENTS

| DE | 15 67 169 A | 8/1970 |
| DE | 16 43 040 A | 4/1971 |

OTHER PUBLICATIONS

International Search Report dated Aug. 21, 2002.

Primary Examiner—Bernard Dentz

(57) ABSTRACT

This invention relates to a process for the preparation of alkyl-N-(3-dimethylamino)alkylcarbamates by reacting an alkyl-chloroformate in an alcohol.

8 Claims, No Drawings

PROCESS FOR THE PREPARATION OF ALKYL-N-(3-DIMETHYLAMINO) ALKYLCARBAMATES

CROSS REFERENCE TO RELATED APPLICATIONS

The present application is a 35 U.S.C. § 371 national phase conversion of PCT/EP02/05456 filed Apr. 18, 2002, which claims priority of European Application No. 01110711.7 filed May 3, 2001 and European Application No. 01113778.3 filed Jun. 6, 2001.

This invention relates to a process for the preparation of alkyl-N-(3-dimethylamino)alkylcarbamates.

Alkyl-N-(3-dimethylamino)alkylcarbamates and their salts can be used as fungicides (see GB 1 212 708, ZA 68 5172, DE 1 567 169, DE 16 43 040).

N-propyl-3-(dimethylamino)n-propylcarbamate is a well known fungicidal active ingredient and is normally sold as the hydrochloride salt. This compound is normally prepared by reacting 3-(dimethylamino)n-propylamine with n-propyl chloroformate in inert solvents including toluene and ethers.

We have now found a new process which is characterised by carrying out the reaction at varying temperatures in alcohols or mixtures of alcohols with water, inert organic solvents or mixtures thereof.

Thus the invention provides a process for the preparation of alkyl-N-(3-dimethylamino)alkylcarbamates which comprises reacting an alkyl-chloroformate in an aliphatic ($C_1$–$C_6$)-alcohol.

Preferably, the process of the present invention is used for the preparation of N-propyl-3-(dimethylamino)n-propylcarbamate by reacting n-propyl chloroformate in an aliphatic ($C_1$–$C_6$)-alcohol.

By using the process of the present invention, it is possible to operate in a wide range of temperatures achieving very high yields.

The fact that this reaction proceeds in such high yields is surprising since the alcohol would be expected to react with the n-propyl chloroformate especially in the presence of an acid acceptor like the 3-(dimethylamino)n-propylamine or n-propyl-3-(dimethylamino)n-propylcarbamate itself, (see for example Houben-Weyl, 4th ed., (1983), E4, page 68).

However, in terms of the n-propyl chloroformate, a yield of 95% can be obtained by using this process and yields based on the amine can be even higher (up to 97%).

As one would infer, the present invention provides high yields of n-propyl-3-(dimethylamino)n-propylcarbamate compared with processes carried out in inert solvents or water (see DE 16 43 040, DE1 567 169, GB 1 212 708, ZA 68 5172) or other standard carbamate processes (e.g. Houben-Weyl, 4th ed., (1983), 8, p. 138ff and E4, p.149ff).

An additional advantage of the process of the invention is that no additional acid acceptor is required.

Another advantage is that the reaction can be carried out in a wide range of temperatures from –20° C. up to the boiling point of the alcohol and even higher, in general up to 200° C.

Preferred temperature is about –20° C. to about 110° C., especially preferred temperature is about –20° C. to about 97° C. These temperatures and therefore reaction speeds are generally significantly higher than in other processes using only inert solvents, water or mixtures thereof (e.g. Houben-Weyl, 4th ed., (1983), 8, p. 138ff and E4, p.149ff).

Often selectivity tends to decrease when using higher temperatures and in the toluene example the degradation of n-propyl chloroformate increases significantly at temperatures higher than 65° C. giving large amounts of carbon dioxide and n-propyl chloride. In other literature examples (see Houben-Weyl, 4th ed. 11/1, p. 985f and E4, p,153f) this degradation is the main reaction even at lower temperatures.

It is surprising that in our process the yield in terms of both compounds can stay stable even at temperatures above 85° C. and that there is generally very limited degradation of n-propyl-chloroformate.

Alcohols used according to the invention are ($C_1$–$C_6$)-, preferably ($C_1$–$C_4$)-aliphatic alcohols. Further preferred alcohols are propanols, especially n-propanol, also in recycled form. It is also preferred to use mixtures of one or more of such alcohols with water or inert organic solvents or mixtures thereof, preferably up to 30% by weight. Examples of inert organic solvents include toluene and ethers, e.g. THF or methyl t-butyl ether.

For the process of the invention, reagents can be used either stoichiometric or in a molar excess up to 50%, preferably up to 10%.

The molar ratio of 3-(dimethylamino)n-propylamine to n-propyl chloroformate is in general 1:0.75–1.5, preferably 1:0.95–1.1.

The process of the present invention is economically and environmentally advantageous due to several other features.

Alcohols, like n-propanol are environmentally and technically unproblematic solvents compared to ethers or dichloromethane or other inert solvents. Redistilled alcohol can be used.

The reaction can be carried out at a high concentration.

The exothermity at the high reaction temperature can be easily controlled.

There is almost no gas evolution during reaction and there is no waste water.

The invention is illustrated in the following example.

EXAMPLE 3-(dimethylamino)n-propylamine (184.4 g) was added dropwise to recycled n-propanol (443.5 g) at 20–40° C. N-propyl chloroformate (227.3 g) was added dropwise over 30–40 minutes. The temperature rose quickly and the flask was easily cooled so that the temperature was maintained at 80–85° C. After distilling off the n-propanol (which is later reused) the residue is n-propyl-3-(dimethylamino)n-propylcarbamate hydrochloride in a yield of 97% based on the 3-(dimethylamino)n-propylamine. This is 4% higher than when the reaction is carried out using toluene.

The yield was 95% based on the n-propyl chloroformate which is at least 16% higher than when the reaction is carried out with toluene.

Example for the Toluene Process n-propyl chloroformate (180 g) was added dropwise to toluene (650 g) at 20–40° C. 3-(dimethylamino)n-propylamine (125 g) was added dropwise over 30–40 minutes. The temperature rose quickly and the flask was cooled so that the temperature was maintained at 55–60° C. The reaction mixture was cooled to 40–45° C. and water was added. After phase separation the crude n-propyl-3-(dimethylamino)n-propylcarbamate solution was distilled to give n-propyl-3-(dimethylamino)n-propylcarbamate hydrochloride in a yield of 93% based on 3-(dimethylamino)n-propylamine.

The yield was 79% based on the n-propyl chloroformate.

What is claimed is:

1. A process for the preparation of an alkyl-N-(3-dimethylamino)alkylcarbamate which comprises reacting an alkyl-chloroformate with a 3-dimethylamino-alkylamine in an aliphatic ($C_1$–$C_6$) alcohol or a mixture of one or more of such an alcohol with up to 30% by weight of water or inert organic solvents or mixtures thereof.

2. A process according to claim 1 for the preparation of n-propyl-3-(dimethylamino)n-propylcarbamate by using n-propyl chloroformate and 3-dimethylamino-propylamine.

3. A process according to claim 2 in which n-propanol or recycled n-propanol is the aliphatic alcohol.

4. A process according to claim 1 wherein the reaction is run in a temperature range from about –20° C. to about 110° C.

5. A process according to claim 1 where both reagents can be used either stoichiometrically or in a molar excess up to 50%.

6. A process according to claim 1 where n-propyl chloroformate is used in a molar excess of up to 10%.

7. A process according to claim 2 wherein the reaction is run in a temperature range from about –20° C. to about 110° C.

8. A process according to claim 3 wherein the reaction is run in a temperature range from about –20° C. to about 110° C.

* * * * *